US00PP25457P2

(12) United States Plant Patent
Zampini

(10) Patent No.: US PP25,457 P2
(45) Date of Patent: Apr. 21, 2015

(54) ***CORNUS* PLANT NAMED 'GOSTMAZAM'**

(50) Latin Name: *Cornus sericea*
Varietal Denomination: Gostmazam

(71) Applicant: James W. Zampini, Fairport Harbor, OH (US)

(72) Inventor: James W. Zampini, Fairport Harbor, OH (US)

(73) Assignee: Lake Country Nursery, Perry, OH (US)

( * ) Notice: Subject to any disclaimer, the term of this patent is extended or adjusted under 35 U.S.C. 154(b) by 103 days.

(21) Appl. No.: 13/815,621

(22) Filed: Mar. 13, 2013

(51) Int. Cl.
*A01H 5/00* (2006.01)

(52) U.S. Cl.
USPC ..... Plt./220

(58) Field of Classification Search
USPC ..... Plt./220
See application file for complete search history.

*Primary Examiner* — Annette Para
(74) *Attorney, Agent, or Firm* — Penny J. Aguirre

(57) ABSTRACT

A new cultivar of *Cornus*, 'Gostmazam', is that characterized by its variegated foliage with green centers and gold to creamy white margins, its stems that are bright coral red in winter, its upright and rounded plant habit, its fruit that is white and blue tinted, its yellowish white flowers, and its vigorous growth habit.

2 Drawing Sheets

Botanical classification: *Cornus sericea.*
Variety denomination: 'Gostmazam'.

BACKGROUND OF THE INVENTION

The present invention relates to a new and distinct cultivar of *Cornus sericea* and will be referred to hereafter by its cultivar name, 'Gostmazam'. 'Gostmazam' is a new cultivar of red twig dogwood, a shrub grown for use as an ornamental landscape plant.

The Inventor discovered the new cultivar as a seedling in a seedbed at his nursery in Perry, Ohio in 2009. The seedbed had been planted with seeds from the *Cornus sericea* cultivar 'Cardinal' (not patented).

Asexual propagation of the new cultivar was first accomplished by the Inventor using stem cuttings in summer of 2009 in Perry, Ohio. Asexual propagation of the new cultivar by stem cuttings has been determined that the characteristics are stable and are reproduced true to type in successive generations.

SUMMARY OF THE INVENTION

The following traits have been repeatedly observed and represent the characteristics of the new cultivar as grown outdoors in a trial plot in Perry, Ohio. These attributes in combination distinguish 'Gostmazam' as unique cultivar of *Cornus.*

1. 'Gostmazam' exhibits variegated foliage with green centers and gold to creamy white margins.
2. 'Gostmazam' exhibits stems that are bright coral red in winter.
3. 'Gostmazam' exhibits an upright and rounded plant habit.
4. 'Gostmazam' exhibits fruit that is white and blue tinted.
5. 'Gostmazam' exhibits yellowish white flowers.
6. 'Gostmazam' exhibits a vigorous growth habit.

The parent plant of 'Gostmazam', 'Cardinal', differs from 'Gostmazam' in having non-variegated green foliage and in having stems that is more red in color rather than coral red.

'Gostmazam' can also be compared to the cultivar of *Cornus alba*, 'Bailhalo' (U.S. Plant Pat. No. 8,722). 'Bailhalo' differs from 'Gostmazam' in having variegated foliage with white margins and in having stems that are darker red in color.

BRIEF DESCRIPTION OF THE DRAWING

The accompanying colored photographs were taken in mid summer and illustrate the overall appearance and distinct characteristics of three year-old plants the new *Cornus* as grown in a garden in Perry, Ohio.

The photograph in FIG. 1 provides a close-up view of the flowers and foliage of 'Gostmazam'.

Figure 1:
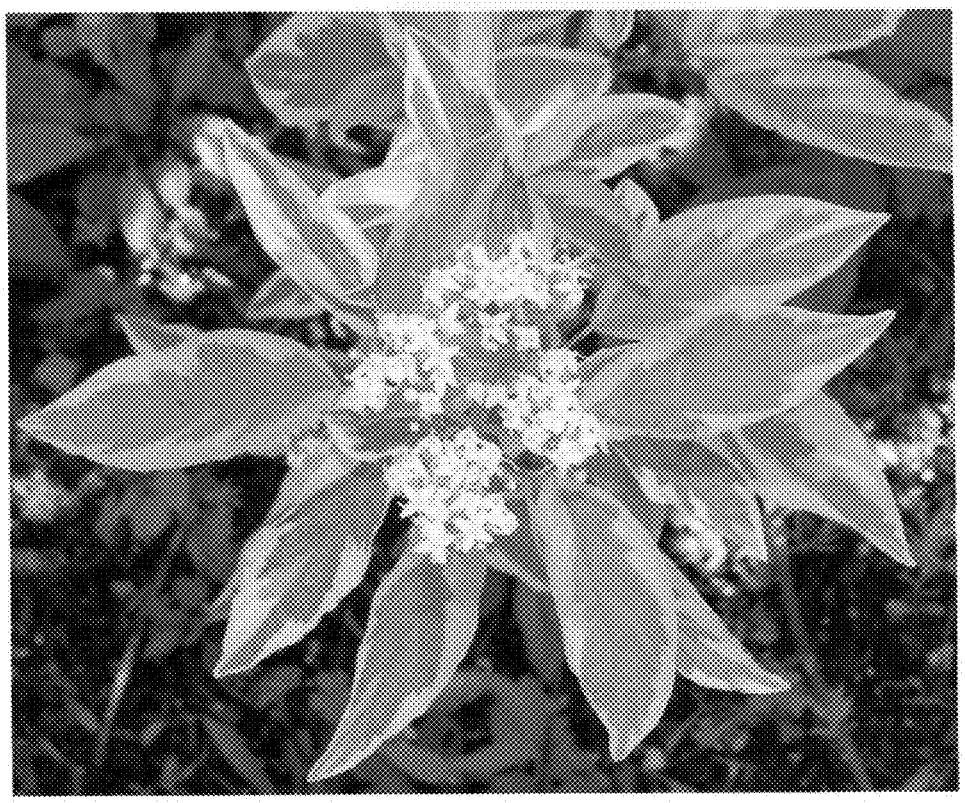
Figure 2:
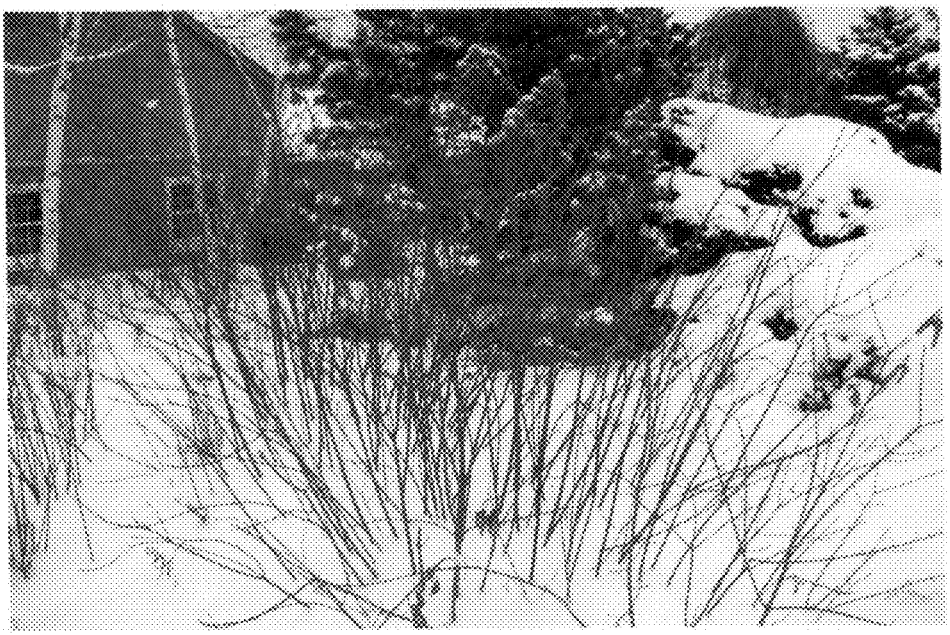

The photograph in FIG. 2 provides a view of the winter stems of 'Gostmazam'.

The colors in the photographs may differ slightly from the color values cited in the detailed botanical description, which accurately describe the colors of the new *Cornus.*

DETAILED BOTANICAL DESCRIPTION

The following is a detailed description of three year-old plants the new *Cornus* as grown in 5-gallon containers in Perry, Ohio. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period.*—Blooms for 3 to 4 weeks in mid May in Ohio.

*Plant type.*—Deciduous shrub.

*Plant habit.*—Upright and rounded, suckering.

*Plant height and spread.*—Reaches 1.2 to 1.5 m in height and 0.9 to 1.2 m in spread.

*Diseases and pests.*—The new cultivar has been observed to be disease free to date under the trial conditions grown.

*Cold hardiness*.—At least in U.S.D.A. Zone 4.

*Root description*.—Fibrous.

*Propagation*.—Softwood (preferred) or hardwood stem cuttings.

*Growth rate*.—Vigorous.

Stem description:

*Shape*.—Oval.

*Stem color*.—New and mature growth 144A and blushed with 165A, winter color 61A.

*Stem size*.—Main branches; up to 5 mm in diameter and 90 cm in length, lateral branches; average of 3 mm in diameter and up to 50 cm in length.

*Stem surface*.—New growth is shiny, mature growth is woody and glabrous.

*Internode length*.—Average of 5 cm, opposite arrangement.

*Branching*.—Basal stems with an average of 6 lateral branches per basal stem.

Foliage description:

*Leaf shape*.—Elliptic.

*Leaf division*.—Simple.

*Leaf base*.—Cuneate.

*Leaf apex*.—Acuminate to Acute.

*Leaf fragrance*.—None.

*Leaf venation*.—Pinnate, not conspicuous, color matches leaf coloration on upper surface and lower surface.

*Leaf margins*.—Slight undulations to entire.

*Leaf arrangement*.—Opposite.

*Leaf attachment*.—Petiolate.

*Leaf surface*.—Glabrous on upper surface and lower surface.

*Leaf internode length*.—Average of 4 cm.

*Leaf color*.—Newly expanded leaves upper and lower surface; ranging between 144A, 146A and 11B, mature leaves upper surface; centers ranging between 144A and 146B with random spots of 144B, margins ranging between 11A and N144B, mature leaves lower surface; centers ranging between 147B to 147C to 138B, margins ranging between 11A and N144A.

*Leaf size*.—Up to 8 cm in length and 3 cm in width.

*Petioles*.—Up to 1 cm in length and 1 mm in width, 144A in color, glabrous surface.

*Stipules*.—Up to 5 mm in length and 1 mm in width, 144A in color.

Inflorescence description:

*Inflorescence type*.—Compound corymb on terminals.

*Inflorescence size*.—An average of 3 cm in length and 5 in diameter.

*Flower buds*.—Oblong-conical in shape, 155B in color with base 144D, an average of 3.5 mm in length and 2 mm in width.

*Flower fragrance*.—None.

*Lastingness of inflorescence*.—Inflorescence blooms for about 10 days with individual flowers lasting about 4 days.

*Flower quantity*.—Average of 130 flowers per inflorescence.

*Flower type*.—Rotate.

*Flower size*.—Average of 7 mm in diameter and 5 mm in depth.

*Peduncles*.—Primary an average of 1.4 cm in length to base of inflorescence and 3 mm in diameter with secondary an average of 1 cm in length and 2 mm in width and tertiary an average of 7 mm in length and 1.5 mm in width, 146C in color, glabrous to slightly pubescent surface, oval in shape.

*Pedicels*.—Average of 2.5 mm in length and 1 mm in diameter, 146C in color, pubescent surface, oval in shape.

*Calyx*.—Closed campanulate in shape, 1.5 mm in diameter and length.

*Sepals*.—4, entirely fused into calyx, 146D in color, finely pubescent surface.

*Petals*.—4, base fused to top of calyx, spreading horizontally, lanceolate in shape, about 2 mm in length and 2 mm in width, margins entire, apex acute, outer and inner surface is glabrous, color of inner and outer surface is NN155B.

Reproductive organs:

*Gynoecium*.—1 pistil, about 2 mm in length, style is about 2 mm in length, and 145D in color, stigma is about 0.5 mm in diameter, globose in shape and 145D in color, ovary is disked shape, about 1.5 mm in diameter and 145D in color.

*Androcoecium*.—4 stamens, about 5 mm in length, all exserted beyond corolla, filaments are 155A in color and about 4 mm in length, anthers are about 1.5 mm in length, dorsifixed, 4B in color, pollen not discernable.

*Fruit and seed*.—True berry, oblong in shape, about 9 mm in length and 6 mm in diameter, present in mid summer, matures to 157D in color with a hint of 97B, seed; 1, 6 mm in length and 4 mm in width in size and 199A in color with a tint of N199B.

It is claimed:

1. A new and distinct cultivar of *Cornus* plant named 'Gostmazam' as herein illustrated and described.

* * * * *